United States Patent
Samuel et al.

(10) Patent No.: US 11,471,493 B2
(45) Date of Patent: Oct. 18, 2022

(54) METHOD FOR TREATING ALLERGIC AIRWAYS DISEASE (AAD)/ASTHMA

(71) Applicant: CYNATA THERAPEUTICS LIMITED, Carlton (AU)

(72) Inventors: Chrishan Samuel, Clayton (AU); Simon Royce, Clayton (AU)

(73) Assignee: CYNATA THERAPEUTICS LIMITED, Carlton (AU)

( * ) Notice: Subject to any disclaimer, the term of this patent is extended or adjusted under 35 U.S.C. 154(b) by 267 days.

(21) Appl. No.: 16/646,041

(22) PCT Filed: Aug. 31, 2018

(86) PCT No.: PCT/AU2018/050937
§ 371 (c)(1),
(2) Date: Mar. 10, 2020

(87) PCT Pub. No.: WO2019/051536
PCT Pub. Date: Mar. 21, 2019

(65) Prior Publication Data
US 2020/0276243 A1    Sep. 3, 2020

(30) Foreign Application Priority Data
Sep. 15, 2017   (AU) .............................. 2017903758

(51) Int. Cl.
*A61K 35/28* (2015.01)
*A61P 11/06* (2006.01)
*C12N 5/0775* (2010.01)
*A61K 9/00* (2006.01)

(52) U.S. Cl.
CPC ............. *A61K 35/28* (2013.01); *A61P 11/06* (2018.01); *C12N 5/0668* (2013.01); *A61K 9/0019* (2013.01); *A61K 9/0043* (2013.01)

(58) Field of Classification Search
None
See application file for complete search history.

(56) References Cited

U.S. PATENT DOCUMENTS

| 2014/0273211 A1 | 9/2014 | Slukvin et al. | |
| 2018/0221411 A1* | 8/2018 | Vesey | C12N 5/0663 |
| 2019/0307811 A1* | 10/2019 | Samuel | A61K 38/2221 |

FOREIGN PATENT DOCUMENTS

| WO | 2017156580 A1 | 9/2017 |
| WO | 2018227244 A1 | 12/2018 |

OTHER PUBLICATIONS

Royce S. et al. iPSC and Mesenchymoangioblast Derived Mesenchymal Stem Cells . . . FASEB 33(5)6402-6411, 2019. (Year: 2019).*
Bloom et al., "A reproducible immunopotency assay to measure mesenchymal stromal cell-mediated T-cell suppression," Cytotherapy, 2015, vol. 17, No. 2, pp. 140-151.
Royce et al., "Combination therapy with relaxin and methylprednisolone augments the effects of either treatment alone in inhibiting subepithelial fibrosis in an experimental model of allergic airways disease," Clinical Science, 2013, vol. 124, pp. 41-51.
Royce et al., "Intranasal administration of mesenchymoangioblast-derived mesenchymal stem cells abrogates airway fibrosis and airway hyperresponsiveness associated with chronic allergic airways disease," The FASEB Journal, 2017, vol. 31, No. 9, pp. 4168-4178.
Royce et al., "Mesenchymal stem cells and serelaxin synergistically abrogate established airway fibrosis in an experimental model of chronic allergic airways disease," Stem Cell Research, 2015, vol. 15, No. 3, pp. 495-505.
Woessner Jr., J. Frederick, "Quantification of Matrix Metalloproteinases in Tissue Samples," Methods in Enzymology, 1995, vol. 248, pp. 510-528.
Extended European Search Report dated Mar. 26, 2021 in corresponding European Patent Application No. 18855341.6 (7 pages).
Battula et al., "Human placenta and bone marrow derived MSC cultured in serum-free, b-FGF-containing medium express cell surface frizzled-9 and SSEA-4 and give rise to multilineage differentiation," Differentiation, 2007, vol. 75, pp. 279-291.
Office Action dated Nov. 3, 2021 in corresponding European Patent Application No. 18855341.6 (6 pages).
Koch et al., "Mesenchymoangioblast-derived mesenchymal stromal cells inhibit cell damage, tissue damage and improved peripheral blood flow following hindlimb ischemic injury in mice," Cytotherapy, 2016, vol. 18, No. 2, pp. 219-228 (10 pages).
Vodyanik et al., "A mesoderm-derived precursor for mesenchymal stem and endothelial cells," Cell Stem Cell, 2010, vol. 7, No. 6, pp. 718-729 (12 pages).
International Search Report and Written Opinion in International PCT Application No. PCT/AU2018/050937, dated Oct. 12, 2018 (11 pages).
Office Action dated Mar. 30, 2022 in corresponding Russian Patent Application No. 2020111190 (10 pages).
English translation of the Office Action dated Mar. 30, 2022 in corresponding Russian Patent Application No. 2020111190 (10 pages).

(Continued)

*Primary Examiner* — Ralph J Gitomer
(74) *Attorney, Agent, or Firm* — Melissa Hunter-Ensor; Leslie Serunian; Greenberg Traurig, LLP (57) ABSTRACT

The invention relates to use of a mesenchymoangioblast-derived mesenchymal stem cell (MSC-MSC) for treating allergic airway disease (AAD)/asthma in a subject.

22 Claims, 5 Drawing Sheets

(56) References Cited

OTHER PUBLICATIONS

Search Report dated Mar. 30, 2022 in corresponding Russian Patent Application No. 2020111190 (2 pages).
English translation of the Search Report dated Mar. 30, 2022 in corresponding Russian Patent Application No. 2020111190 (2 pages).

* cited by examiner

METHOD FOR TREATING ALLERGIC AIRWAYS DISEASE (AAD)/ASTHMA

CROSS REFERENCE TO RELATED APPLICATIONS

This application is the U.S. National Stage Application, pursuant to 35 U.S.C. § 371, of International PCT Application No. PCT/AU2018/050937, filed on Aug. 31, 2018, which designated the United States and published in English, and which claims priority to Australian Application No. 2017903758, filed on Sep. 15, 2017, the contents of all of which are incorporated herein by reference in their entireties.

FIELD

The invention relates to treating allergic airways disease (AAD)/asthma in a subject.

BACKGROUND

Asthma is a chronic respiratory disease affecting approximately 300 million people worldwide, attributing to 250 000 annual deaths. There are three main components to its pathogenesis: airway inflammation (AI); airway remodelling (AWR; representing structural changes in the airways/lung that eventually lead to airway fibrosis and obstruction); and airway hyperresponsiveness (AHR; the clinical feature of asthma). AWR can result from persistent or chronic AI, but can also develop and contribute to AHR independently of AI.

Current asthma therapy, including corticosteroids and β-agonists, is focused on symptom management, rather than disease regression, and is therefore not fully effective. Subjects treated with β-agonist-based therapies have relief of their asthma symptoms, but their underlying AI persists. As such, subjects requiring chronic use of β-agonists are at a greater risk of serious worsening of asthma, leading to hospitalisation and death.

The gold-standard therapy of corticosteroids is also ineffective in treating the severe and severe-refractory subpopulations of asthmatic subjects. Severe asthmatic subjects often need treatment with high doses of corticosteroids that can be associated with systemic side-effects and do not necessarily improve lung function or quality of life. Additionally, the severe refractory sub-group of asthmatic subjects show a fixed airway restriction, and therefore this population displays the critical role of AWR as part of their asthma symptoms, highlighting an urgent need for treatment strategies that can target and reduce AWR.

Mesenchymal stem cells (MSCs) are multipotent stromal cells that have the capacity to divide into a number of cell lineages. These cells express Class I major histocompatibility complex (MHC-I), but lack MHC-II and co-stimulatory molecules CD80, CD86 and CD40, and hence, are immunoprivileged. As such, MSCs can be administered systemically via intravenous (IV) infusion allowing for a broad distribution. Upon IV administration, MSCs accumulate in the lung. MSCs also home to the injured tissue through the expression of the chemokine receptor type 4, expression of which is heightened in a pro-inflammatory environment, as in asthma, enhancing their homing ability.

Murine models of allergic airways disease (AAD), which mimic several features of human asthma, have been used to show that MSCs exhibit immunomodulatory and anti-inflammatory properties through both direct cell-cell contact and secretion of paracrine factors. Administration of exogenous MSCs was shown to decrease Th2 proliferation and reduce the Th2 bias, which contributes to AAD. Suppression of dendritic cell activation, migration and antigen presentation has been observed. A decrease in eosinophil-associated pro-inflammatory cytokines was observed in bronchoalveolar lavage fluid. Compared to corticosteroids which suppress AI, MSCs have been shown in these models to actively reduce the presence and activity of the cells responsible for inflammation.

Furthermore, MSC treatment has been shown to reduce epithelial thickness, smooth muscle hyperplasia and goblet cell metaplasia in the airways, and modestly decrease sub-epithelial and total collagen deposition (fibrosis) through their ability to promote collagen-degrading gelatinase levels, suggesting that MSCs also have anti-remodelling actions.

However, MSCs have not consistently demonstrated relief of the adverse symptoms associated with chronic disease settings, and the outcomes of MSC treatment can vary depending on their tissue origin/source, extent of culture expansion, donor-dependent viability and efficacy, and the timing of their administration.

Furthermore, MSCs have only demonstrated beneficial effects when administered in combination with a second therapeutic agent.

Additionally, as only a relatively small number of MSCs can be isolated from each donor organ, a continuous supply of donors would be needed to facilitate sufficient numbers for experimental and commercial use.

It is to be understood that if any prior art publication is referred to herein, such reference does not constitute an admission that the publication forms a part of the common general knowledge in the art in Australia or any other country.

SUMMARY

A first aspect provides a method for treating AAD/asthma in a subject, the method comprising administering a mesenchymoangioblast mesenchymal stem cell (MCA-MSC) to the subject, wherein the MCA-MSC expresses miR-145-5p, miR-181b-5p, and miR-214-3p, but not miR-127-3p and miR-299-5p.

An alternative or additional embodiment of the first aspect provides use of a mesenchymoangioblast mesenchymal stem cell (MCA-MSC) in the manufacture of a medicament for treating AAD/asthma in a subject, wherein the MCA-MSC expresses miR-145-5p, miR-181b-5p, and miR-214-3p, but not miR-127-3p and miR-299-5p.

A further alternative or additional embodiment of the first aspect provides a mesenchymoangioblast mesenchymal stem cell (MCA-MSC) for use in a method of treating AAD/asthma in a subject, wherein the MCA-MSC expresses miR-145-5p, miR-181b-5p, and miR-214-3p, but not miR-127-3p and miR-299-5p.

In one embodiment, the MCA-MSC has a $CD73^+CD105^+CD90^+CD146^+CD44^+CD10^+CD31^-CD45^-$ phenotype.

In one embodiment the MCA-MSC is made by a method comprising:
(a) culturing a primitive mesoderm cell in a mesenchymal-colony forming medium (M-CFM) comprising LiCl and FGF2, but excluding PDGF, under normoxic conditions for sufficient time for a mesenchymal colony to form; and
(b) culturing the mesenchymal colony of (a) adherently to produce the MCA-MSC.

In one embodiment, the MCA-MSC is administered intravenously or intranasally. In one embodiment, the MCA-MSC is administered intranasally.

In one embodiment, treating comprises administering about $1\times10^6$ to about $1\times10^9$ MCA-MSCs to the subject.

In one embodiment, the subject is mammalian. In one embodiment, the subject is human.

In one embodiment, the subject has previously been administered a corticosteroid or a β agonist for treating asthma. In another embodiment, the subject has not previously been administered a corticosteroid or a β agonist for treating asthma.

In one embodiment, the subject is not administered a corticosteroid or a β-agonist.

In one embodiment, the subject has severe asthma or severe-refractory asthma.

In one embodiment, treating AAD/asthma or a characteristic feature thereof comprises:

(a) decreasing AI, AWR, airway fibrosis, lung fibrosis, goblet cell metaplasia, epithelial thickening, airway transforming growth factor (TGF)-β1 level, subepithelial myofibroblast density, subepithelial collagen concentration, or total lung collagen concentration; or (b) increasing lung matrix metalloproteinase (MMP) activity; or (c) any combination of any one or more feature of (a) or any combination of any one or more feature of (a) and (b).

Use of MCA-MSCs to treat AAD/asthma or a characteristic feature thereof may provide one or more of the following non-limiting advantages:

substantial if not complete reversal of aberrant airway TGF-β1 levels, airway/lung fibrosis and AHR
increased collagen-degrading MMP levels
no effect on basal expression of the parameters measured, indicating a safe and effective treatment of AAD/asthma.

The solution provided by the invention was unexpected because previous studies showed that ovalbumin (OVA)-induced promotion of subepithelial and total collagen deposition could only be fully reversed when stem cell-based treatments were administered in combination with an antifibrotic drug. Therefore, the present invention provides a significant improvement in treating AAD/asthma.

BRIEF DESCRIPTION OF THE FIGURES

FIG. 8 shows effects of MCA-MSCs on AHR according to Example 4. Airway resistance (reflecting changes in AHR) was assessed via invasive plethysmography in response to increasing doses of nebulized methacholine (a bronchoconstrictor; and expressed as resistance change from baseline). Shown is the mean±SEM airway resistance to each dose of methacholine tested, from n=7-8 mice/group. *P<0.05, ***P<0.001 vs saline (SAL) group; ##P<0.01, ###P<0.001 vs OVA group; ¶¶P<0.01 vs OVA MCA-MSC IV group.

DETAILED DESCRIPTION

Structural changes known as airway remodelling (AWR) characterise chronic/severe asthma and contribute to lung dysfunction. In general, asthma is managed with corticosteroids and/or β-agonists.

The present invention relates to treating asthma in a subject using MCA-MSCs, which is an improvement over asthma treatment with corticosteroids and/or β agonists and is an improvement over suggested treatment with MSCs in combination with other agents.

Examples 1 and 2 demonstrate differentiation of human induced pluripotent stem cells (iPSCs) into precursor cells known as mesenchymoangioblasts (MCAs), a class of early clonal mesoendodermal precursor cells, and subsequently into mesenchymal stem cells (MCA-MSCs). As iPSCs can proliferate indefinitely, and MCAs themselves can expand into extremely large quantities of MSCs, sufficient MCA-MSCs can be acquired from a single Master Cell Bank of iPSCs-derived from a single healthy blood donor, thereby limiting donor-dependent and expansion-dependent variability and contamination from non-target cells, without the need for excessive culture expansion once MSCs are formed.

The MCA-MSCs of the disclosure provide the advantages of essentially unlimited supply and the further advantage of improved immunomodulatory effects compared with MSCs of the prior art.

In this disclosure, in particular in Examples 4 and 5, the therapeutic potential of these MCA-MSCs when delivered to a well-established murine model of chronic AAD was investigated. This murine model of AAD presents with the three central features of human asthma, AI, AWR and AHR, and is accepted in the art as a pre-clinical model of asthma. In particular, the anti-remodelling effects of intravenous (IV)-administered vs intranasal (IN)-administered MCA-MSCs were compared.

Importantly, although some MSCs may have shown some efficacy in treating asthma or its symptoms, such effects have only been obtained when those MSCs have been used in combination with other therapeutic agents. Advantageously, the present invention avoids the need for combination therapy.

Asthma

Asthma and/or AAD may be characterised by any one or more of the following features in any combination: AI, AWR, AHR, airway/lung fibrosis, goblet cell metaplasia, epithelial thickening, increased airway transforming growth factor (TGF)-β1 levels, absent or low lung MMP-9 levels, increased subepithelial myofibroblast density, subepithelial collagen accumulation, and total lung collagen accumulation.

Accordingly, treatment of asthma and/or AAD with MCA-MSCs of the disclosure may be characterised by treating any one or more of the following features in any combination: decreased AI, decreased AWR, decreased airway/lung fibrosis, decreased goblet cell metaplasia, decreased epithelial thickening, decreased airway transforming growth factor (TGF)-β1 levels, subepithelial myofibroblast and collagen reduction, and decreased total lung collagen concentration.

Treatment of AAD/asthma with MCA-MSCs of the disclosure may increase expression/activity of an MMP, for example a gelatinase and/or a collagenase. In one embodiment, the MMP is MMP-9. In another embodiment, the MMP is MMP13. In another embodiment, the MMP is MMP1, MMP2, MMP3, MMP7, MMP8, or MMP12.

Mesenchymoagioblast-Mesenchymal Stem Cells (MCA-MSCs)

Accordingly, the invention provides an improved therapy for AAD/asthma, or one or more of its characteristic features, by administering MCA-MSCs. MCA-MSCs exert their effects through their immunomodulatory properties and are able to act directly at the site producing a characteristic feature of AAD/asthma.

MCA-MSCs secrete bioactive molecules such as cytokines, chemokines and growth factors and have the ability to modulate the immune system. MCA-MSCs have been shown to facilitate regeneration and effects on the immune system without relying upon engraftment. In other words, the MCA-MSCs themselves do not necessarily become incorporated into the host subject—rather, they exert their effects and are then eliminated within a short period of time. However, MCA-MSCs may be engrafted.

As used herein, "mesenchymal stem cell" or "MSC" refers to a particular type of stem cell that may be isolated from a wide range of tissues, including bone marrow, adipose tissue (fat), placenta and umbilical cord blood. Alternatively, MSCs may be produced from pluripotent stem cells (PSCs). MSCs are also known as "mesenchymal stromal cells".

As used herein, "MCA-MCS" refers to a particular type of MSCs produced from iPSCs via a mesenchymoangioblast phenotype. Production of MCA-MSCs from PSCs is described in international patent application no. PCT/AU2017/050228 filed 14 Mar. 2017, which is incorporated in full by this cross-reference, and is described in Examples 1 and 2. MCA-MSCs are distinct from MSCs of the prior art, for example as demonstrated in Example 3.

MSCs have been shown to exert immunomodulatory activities against T cells, B cells, dendritic cells, macrophages, and natural killer cells. While not wishing to be bound by theory, the underlying mechanisms may comprise immunomodulatory mediators, for example nitric oxide, indoleamine 2,3, dioxygenase, prostaglandin E2, tumour necrosis factor-inducible gene 6 protein, CCL-2, and programmed death ligand 1. These mediators are expressed at a low level until stimulated, for example by an inflammatory cytokines, such as IFNγ, TNFα, and IL-17.

As used herein, "pluripotent stem cell" or "PSC" refers to a cell that has the ability to reproduce itself indefinitely, and to differentiate into any other cell type. There are two main types of PSC: embryonic stem cells (ESCs); and induced pluripotent stem cells (iPSCs).

As used herein, "embryonic stem cell" or "ESC" refers to a cell isolated from a five to seven day-old embryo donated with consent by subjects who have completed in vitro fertilisation therapy, and have surplus embryos. The use of ESCs has been hindered to some extent by ethical concerns about the extraction of cells from human embryos.

Suitable human PSCs include H1 and H9 human embryonic stem cells.

As used herein, "induced pluripotent stem cell" or "iPSC" refers to an ESC-like cell derived from adult cells. iPSCs have very similar characteristics to ESCs, but avoid the ethical concerns associated with ESCs, since iPSCs are not derived from embryos. Instead, iPSCs are typically derived from fully differentiated adult cells that have been "reprogrammed" back into a pluripotent state.

Suitable human iPSCs include, but are not limited to, iPSC 19-9-7T, MIRJT6i-mND1-4 and MIRJT7i-mND2-0 derived from fibroblasts and iPSC BM119-9 derived from bone marrow mononuclear cells. Other suitable iPSCs may be obtained from Cellular Dynamics International (CDI) of Madison, Wis., USA.

In one embodiment, MCA-MSCs used according to the invention are formed from primitive mesodermal cells. The primitive mesoderm cells may have mesenchymoangioblast (MCA) potential. The primitive mesoderm cells may have a $^{EMH}lin^-KDR^+APLNR^+PDGFRalpha^+$ phenotype. In one embodiment, MCA-MSCs used according to the invention are formed from $^{EMH}lin^- KDR^+APLNR^+PDGFRalpha^+$ primitive mesoderm cells with MCA potential.

As used herein, "$^{EMH}lin^-KDR^+APLNR^+PDGFRalpha^+$ primitive mesoderm cell with MCA potential" refers to a cell expressing typical primitive streak and lateral plate/extra-embryonic mesoderm genes. These cells have potential to form MCA and hemangioblast colonies in serum-free medium in response to fibroblast growth factor 2 (FGF2). When cultured according to Example 2, these cells become MCA-MSCs.

The term $^{EMH}lin^-$ denotes lack of expression of CD31, VE-cadherin endothelial markers, CD73 and CD105 mesenchymal/endothelial markers, and CD43 and CD45 hematopoietic markers.

In one embodiment, MCA-MSCs used according to the invention exhibit a $CD73^+CD105^+CD90^+CD146^+CD44^+CD10^+CD31^-CD45^-$ phenotype.

In one embodiment, MCA-MSCs used according to the invention express each of the microRNAs miR-145-5p, miR-181b-5p, and miR-214-3p, but not miR-127-3p and miR-299-5p.

In addition to their effects in treating AAD/asthma demonstrated herein, MCA-MSCs possess "immunomodulatory activities" that may be assessed in vitro as the capacity of a MCA-MSC to suppress proliferation of T helper (CD4$^+$) lymphocytes. Immunomodulatory activities may be quantified in vitro relative to a reference, for example as determined using an ImmunoPotency Assay.

A suitable ImmunoPotency Assay uses an irradiated test MCA-MSC produced according to the method disclosed herein and an irradiated reference sample MSC, which are plated separately at various concentrations with carboxyfluorescein succinimidyl ester-labelled leukocytes purified from healthy donor peripheral blood. T helper (CD4$^+$) lymphocytes that represent a subset of the reference sample are stimulated by adding CD3 and CD28 antibodies. CD4 labelled T cells are enumerated using flow cytometry to assess T cell proliferation. IC50 values are reported as a function of the reference sample. A higher IC50 value indicates a greater magnitude of suppression of proliferation of T helper (CD4$^+$) lymphocytes and thus is indicative of superior T-cell immunomodulatory properties. MSC samples are irradiated prior to use in this assay to eliminate the confounding factor of their proliferative potential.

Treating AAD/Asthma with MCA-MSCs

It will be appreciated by the person skilled in the art that the exact manner of administering to a subject a therapeutically effective amount of MCA-MSCs for treating AAD/asthma in a subject will be at the discretion of the medical practitioner. The mode of administration, including dose, combination with other agents, timing and frequency of administration, and the like, may be affected by the subject's condition and history.

Although it is an advantage of the invention that the MCA-MSCs may be used alone to treat AAD/asthma or a characteristic feature thereof, it will be appreciated that the MCA-MSCs may be combined with another asthma therapy. For example, a medical practitioner may yet treat an asthmatic subject with another asthma therapy when the asthmatic subject has an existing asthma treatment regimen, for example, comprising a corticosteroid or β-agonist therapy, and treatment with MCA-MSCs occurs subsequently.

The MCA-MSC may be administered as a therapeutic composition. As used herein, the term "therapeutic composition" refers to a composition comprising a MCA-MSC or population of MCA-MSCs as described herein that has been formulated for administration to a subject. Preferably, the therapeutic composition is sterile. In one embodiment, the therapeutic composition is pyrogen-free.

In one embodiment, the MCA-MSC or therapeutic composition is provided in a container, preferably a sterile container, preferably a pyrogen-free container. In one embodiment, the container is a syringe, for example suitable for bolus administration. In another embodiment, the container is an infusion bag suitable for infusion. In another embodiment, the container is adapted for IN administration.

The MCA-MSC will be formulated, dosed, and administered in a fashion consistent with good medical practice. Factors for consideration in this context include the particular type of disorder being treated and anticipated side effects or symptoms, the particular subject being treated, the clinical condition of the subject, the site of administration, the method of administration, the scheduling of administration, and other factors known to medical practitioners. The therapeutically effective amount of the MCA-MSCs to be administered will be governed by such considerations.

Doses of MCA-MSCs may range from about $10^3$ cells/m$^2$ to about $10^{11}$ cells/m$^2$, for example about $10^6$ cells/m$^2$ to about $2\times10^8$ cells/m$^2$, or about $10^3$ cells/m$^2$, about $5\times10^3$ cells/m$^2$, about $10^4$ cells/m$^2$, about $5\times10^4$ cells/m$^2$, about $10^5$ cells/m$^2$, about $5\times10^5$ cells/m$^2$, about $10^6$ cells/m$^2$, about $5\times10^6$ cells/m$^2$, about $10^7$ cells/m$^2$, about $5\times10^7$ cells/m$^2$, about $10^8$ cells/m$^2$, about $5\times10^8$ cells/m$^2$, about $10^9$ cells/m$^2$, about $5\times10^9$ cells/m², about $10^{10}$ cells/m², about $5\times10^{10}$ cells/m², or about $10^{11}$ cells/m².

Doses of MCA-MSCs may range from about $10^3$ cells/kg to about $10^{11}$ cells/kg, for example about $10^6$ cells/kg to about $2\times10^8$ cells/kg, or about $10^3$ cells/kg, about $5\times10^3$ cells/kg, about $10^4$ cells/kg, about $5\times10^4$ cells/kg, about $10^5$ cells/kg, about $5\times10^5$ cells/kg, about $10^6$ cells/kg, about $5\times10^6$ cells/kg, about $10^7$ cells/kg, about $5\times10^7$ cells/kg, about $10^8$ cells/kg, about $5\times10^8$ cells/kg, about $10^9$ cells/kg, about $5\times10^9$ cells/kg, about $10^{10}$ cells/kg, about $5\times10^{10}$ cells/kg, or about $10^{11}$ cells/kg.

Doses of MCA-MSCs may range from about $10^3$ cells to about $10^{11}$ cells, for example about $10^6$ cells to about $2\times10^8$ cells, or about $10^3$ cells, about $5\times10^3$ cells, about $10^4$ cells, about $5\times10^4$ cells, about $10^5$ cells, about $5\times10^5$ cells, about $10^6$ cells, about $5\times10^6$ cells, about $10^7$ cells, about $5\times10^7$ cells, about $10^8$ cells, about $5\times10^8$ cells, about $10^9$ cells, about $5\times10^9$ cells, about $10^{10}$ cells, about $5\times10^{10}$ cells, or about $10^{11}$ cells.

The term "therapeutically effective amount" refers to an amount of MCA-MSCs effective to treat in a subject.

The MCA-MSCs may be administered in a single dose, a split dose, or in multiple doses. For example, a split dose may be administered between a subject's nostrils, for example approximately one half of a dose per nostril.

A subject may be administered 1, 2, 3, 4, 5, 6, 7, 8, 9, or 10 doses of MCA-MSCs.

A subject may be administered two or more doses of MCA-MSCs 1 week, 2 weeks, 1 month, or 2 months apart. A subject may be administered two or more doses quarterly, biannually, annually, biennially, or at a greater interval, for example, if AAD/asthma or a characteristic feature thereof recurs in a subject already treated with a MCA-MSC, at or after the time of recurrence.

MCA-MSCs may be administered systemically or peripherally by any suitable route, for example by routes including intravenous (IV), intranasal (IN), intratracheal, intrapulmonary, and intraarterial. In one embodiment, MCA-MSCs are administered by the IV, IN, intratracheal or intrapulmonary route. In one embodiment, MCA-MSCs are administered IN.

In one embodiment, MCA-MSCs are pre-treated prior to administration. Pre-treatment may be with a growth factor or by gene editing, for example, where a growth factor may prime the MCA-MSC and gene editing may confer a new therapeutic property on the MCA-MSC.

The MCA-MSCs may be administered to the subject before, during or after development of AAD/asthma or a characteristic feature thereof by the subject.

As such, the terms "treat", "treating" or "treatment" refer to both therapeutic treatment and prophylactic or preventative measures, wherein the aim is to prevent, reduce, or ameliorate AAD/asthma or a characteristic feature thereof in a subject or slow down (lessen) progression of AAD/asthma or a characteristic feature thereof in a subject. Subjects in need of treatment include those already with AAD/asthma or a characteristic feature thereof as well as those in which AAD/asthma or a characteristic feature thereof is to be prevented or ameliorated.

The terms "preventing", "prevention", "preventative" or "prophylactic" refers to keeping AAD/asthma or a characteristic feature thereof from occurring, or to hinder, defend from, or protect from the occurrence of AAD/asthma or a characteristic feature thereof. A subject in need of prevention AAD/asthma or a characteristic feature thereof may be prone to develop AAD/asthma or a characteristic feature thereof, for example because of family history.

The term "ameliorate" or "amelioration" refers to a decrease, reduction or elimination of AAD/asthma or a characteristic feature thereof.

Treating AAD/asthma or a characteristic feature thereof by administering a MCA-MSC may result in about a 1% decrease, about a 2% decrease, about a 3% decrease, about a 4% decrease, about a 5% decrease, about a 6% decrease, about a 7% decrease, about an 8% decrease, about a 9% decrease, about a 10% decrease, about a 15% decrease, about a 20% decrease, about a 25% decrease, about a 30% decrease, about a 35% decrease, about a 40% decrease, about a 45% decrease, about a 50% decrease, about a 55% decrease, about a 60% decrease, about a 65% decrease, about a 70% decrease, about a 75% decrease, about an 80% decrease, about an 85% decrease, about a 90% decrease, about a 95% decrease, about a 99% decrease, or about a 100% decrease in AAD/asthma or a characteristic feature thereof.

In one embodiment, treating AAD/asthma or a characteristic feature thereof by administering a MCA-MSC may decrease the AAD/asthma or a characteristic feature thereof to a magnitude equivalent to that of a subject who does not have AAD/asthma or a characteristic feature thereof.

The person skilled in the art will readily understand how to assess and quantify AAD/asthma or a characteristic feature thereof, and be able to do so without difficulty or undue burden, for example using methods set out in the present examples. For instance, the following may be quantified: i) inflammation score as a measure of AI; ii) goblet cell metaplasia as a measure of AI-induced AWR; iii) epithelial thickness as a measure of AWR; iv) sub-epithelial collagen thickness as a measure of AWR/fibrosis; v) total lung collagen concentration as a measure of AWR/fibrosis; vi) epithelial TGF-β1 staining as a measure of AWR; vii) subepithelial myofibroblast density as a measure of AWR; viii) gelatinase (e.g. MMP-2 and/or MMP-9) and/or collagenase (e.g. MMP-1 and/or MMP-13) expression/activity as a measure of AWR; and/or ix) airway hyperresponsiveness/reactivity as a measure of lung function and AHR.

Any quantification of AAD/asthma or a characteristic feature thereof may be compared to a control, for example a healthy control subject or healthy population of control subjects who do not have AAD/asthma or a characteristic feature thereof. Alternatively, the control may be a control subject or population of control subjects who had AAD/asthma or a characteristic feature thereof and have been treated with and responded to MCA-MSCs.

As used herein, the term "subject" may refer to a mammal. The mammal may be a primate, particularly a human, or may be a domestic, zoo, or companion animal. Although it is particularly contemplated that the method disclosed herein is suitable for medical treatment of humans, it is also applicable to veterinary treatment, including treatment of domestic animals such as horses, cattle and sheep, companion animals such as dogs and cats, or zoo animals such as felids, canids, bovids and ungulates.

Unless defined otherwise in this specification, technical and scientific terms used herein have the same meaning as commonly understood by the person skilled in the art to which this invention belongs and by reference to published texts.

It is to be noted that the term "a" or "an" refers to one or more, for example, "a MCA-MSC," is understood to represent one or more MCA-MSCs. As such, the terms "a" or "an", "one or more," and "at least one" may be used interchangeably herein.

In the claims which follow and in the description of the invention, except where the context requires otherwise due to express language or necessary implication, the word "comprise" or variations such as "comprises" or "comprising" is used in an inclusive sense, i.e. to specify the presence of the stated features, but not to preclude the presence or addition of further features in various embodiments of the invention.

The term "about" as used herein contemplates a range of values for a given number of ±25% the magnitude of that number. In other embodiments, the term "about" contemplates a range of values for a given number of ±20%, ±15%, ±10%, or ±5% the magnitude of that number. For example, in one embodiment, "about 3 grams" indicates a value of 2.7 grams to 3.3 grams (i.e. 3 grams±10%), and the like.

Similarly, the timing or duration of events may be varied by at least 25%. For example, while a particular event may be disclosed in one embodiment as lasting one day, the event may last for more or less than one day. For example, "one day" may include a period of about 18 hours to about 30 hours. In other embodiments, periods of time may vary by ±20%, ±15%, ±10%, or ±5% of that period of time. The following examples assist in describing the invention, which is not to be limited to such examples.

EXAMPLES

Example 1. Reagents for MCA-MSC Production

TABLE 1

| Reagents | |
| --- | --- |
| Description | Vendor/Cat # or Ref # |
| DMEM/F12 Base Medium | Invitrogen/A1516901 |
| E8 supplement | Invitrogen/A1517101 |
| vitronectin | Life Technologies/A14700 |
| collagen IV | Sigma/C5533 |
| H-1152 ROCK Inhibitor | EMD Millipore/555550 |
| Y27632 dihydrochloride ROCK Inhibitor | Tocris/1254 |
| FGF2 | Waisman Biomanufacturing/WC-FGF2-FP |
| human endothelial-SFM | Life Technologies/11111-044 |
| stemline II hematopoietic stem cell expansion medium | Sigma/S0192 |
| GLUTAMAX | Invitrogen/35050-061 |
| insulin | Sigma/I9278 |
| lithium chloride (LiCl) | Sigma/L4408 |
| collagen I solution | Sigma/C2249 |
| fibronectin | Life Technologies/33016-015 |
| DMEM/F12 | Invitrogen/11330032 |
| recombinant human BMP4 | Peprotech/120-05ET |
| activin A | Peprotech/120-14E |
| Iscove's modified Dulbecco's medium (IMDM) | Invitrogen/12200036 |
| Ham's F12 nutrient mix | Invitrogen/21700075 |
| sodium bicarbonate | Sigma/S5761 |
| L-ascorbic acid 2-phosphate $Mg^{2+}$ | Sigma/A8960 |
| 1-thioglycerol | Sigma/M6145 |
| sodium selenite | Sigma/S5261 |
| non-essential amino acids | HyClone/SH30853.01 |
| chemically defined lipid concentrate | Invitrogen/11905031 |
| embryo transfer grade water | Sigma/W1503 |
| polyvinyl alcohol (PVA) | MP Bio/151-941-83 |
| holo-transferrin | Sigma/TO665 |
| ES-CULT M3120 | Stem Cell Technologies/03120 |
| STEMSPAN serum-free expansion medium (SFEM) | Stem Cell Technologies/09650 |
| L-ascorbic acid | Sigma/A4544 |
| Platelet-derived growth factor subunit B homodimer (PDGF-BB) | Peprotech/110-14B |

The reagents listed in Table 1 are known to the person skilled in the art and have accepted compositions, for example IMDM and Ham's F12. GLUTAMAX comprises L-alanyl-L-glutamine dipeptide, usually supplied at 200 mM in 0.85% NaCl. GLUTAMAX releases L-glutamine upon cleavage of the dipeptide bond by the cells being cultured. Chemically defined lipid concentrate comprises arachidonic acid 2 mg/L, cholesterol 220 mg/L, DL-alpha-tocopherol acetate 70 mg/L, linoleic acid 10 mg/L, linolenic acid 10 mg/L, myristic acid 10 mg/L, oleic acid 10 mg/L, palmitic acid 10 mg/L, palmitoleic acid 10 mg/L, pluronic F-68 90 g/L, stearic acid 10 mg/L, TWEEN 80® 2.2 g/L, and ethyl alcohol. H-1152 and Y27632 are highly potent, cell-permeable, selective ROCK (Rho-associated coiled coil forming protein serine/threonine kinase) inhibitors.

TABLE 2

IF6S medium (10X concentration)

| 10X IF6S | Quantity | Final Concentration |
| --- | --- | --- |
| IMDM | 1 package, powder for 1 L | 5X |
| Ham's F12 nutrient mix | 1 package, powder for 1 L | 5X |
| sodium bicarbonate | 4.2 g | 21 mg/mL |
| L-ascorbic acid 2-phosphate $Mg^{2+}$ | 128 mg | 640 µg/mL |
| 1-thioglycerol | 80 µL | 4.6 mM |
| sodium selenite (0.7 mg/mL solution) | 24 µL | 84 ng/mL |
| GLUTAMAX | 20 mL | 10X |
| non-essential amino acids | 20 mL | 10X |
| chemically defined lipid concentrate | 4 mL | 10X |
| embryo transfer grade water | To 200 mL | NA |

TABLE 3

IF9S medium (1X concentration; based on IF6S)

| IF9S | Quantity | Final Concentration |
| --- | --- | --- |
| IF6S | 5 mL | 1X |
| polyvinyl alcohol (PVA; 20 mg/mL solution) | 25 mL | 10 mg/mL |
| holo-transferrin (10.6 mg/mL solution) | 50 µL | 10.6 µg/mL |
| insulin | 100 µL | 20 µg/mL |
| embryo transfer grade water | To 50 mL | NA |

TABLE 4

Differentiation medium (1X concentration; based on IF9S)

| Differentiation Medium | Quantity | Final Concentration |
| --- | --- | --- |
| IF9S | 3 6 mL | 1X |
| FGF2 | 1.8 µg | 50 ng/mL |
| LiCl (2M solution) | 36 µL | 2 mM |
| BMP4 (100 µg/mL solution) | 18 µL | 50 ng/mL |
| Activin A (10 mg/mL solution) | 5.4 µL | 1.5 ng/mL |

TABLE 5

Mesenchymal colony forming medium (1X concentration)

| Mesenchymal colony forming medium (M-CFM) | Quantity | Final Concentration |
|---|---|---|
| ES-CULT M3120 | 40 mL | 40% |
| STEMSPAN SFEM | 30 mL | 30% |
| human endothelial-SFM | 30 mL | 30% |
| GLUTAMAX | 1 mL | 1X |
| L-ascorbic acid (250 mM solution) | 100 μL | 250 μM |
| LiCl (2M solution) | 50 μL | 1 mM |
| 1-thioglycerol (100 mM solution) | 100 μL | 100 μM |
| FGF2 | 600 ng | 20 ng/mL |

TABLE 6

Mesenchymal serum-free expansion medium (1X concentration)

| Mesenchymal serum-free expansion medium (M-SFEM) | Quantity | Final Concentration |
|---|---|---|
| human endothelial-SFM | 5 L | 50% |
| STEMLINE II HSFM | 5 L | 50% |
| GLUTAMAX | 100 mL | 1X |
| 1-thioglycerol | 87 μL | 100 μM |
| FGF2 | 100 μg | 10 ng/mL |

Example 2. Differentiating Human iPSCs into MCA-MSCs

1. Thawed iPSCs in E8 Complete Medium (DMEM/F12 Base Medium+E8 Supplement)+1 μM H1152 on Vitronectin coated (0.5 μg/cm$^2$) plastic ware. Incubated plated iPSCs at 37° C., 5% $CO_2$, 20% $O_2$ (normoxic).
2. Expanded iPSCs three passages in E8 Complete Medium (without ROCK inhibitor) on Vitronectin coated (0.5 μg/cm$^2$) plastic ware and incubated at 37° C., 5% $CO_2$, 20% $O_2$ (normoxic) prior to initiating differentiation process.
3. Harvested and seeded iPSCs as single cells/small colonies at 5×10$^3$ cells/cm$^2$ on Collagen IV coated (0.5 μg/cm$^2$) plastic ware in E8 Complete Medium+10 μM Y27632 and incubated at 37° C., 5% $CO_2$, 20% $O_2$ (normoxic) for 24 h.
4. Replaced E8 Complete Medium+10 μM Y27632 with Differentiation Medium and incubated at 37° C., 5% $CO_2$, 5% $O_2$ (hypoxic) for 48 h to produce primitive mesoderm cells.
5. Harvested colony forming primitive mesoderm cells from Differentiation Medium adherent culture as a single cell suspension, transferred to M-CFM suspension culture and incubated at 37° C., 5% $CO_2$, 20% $O_2$ (normoxic) for 12 days, until mesenchymal colonies formed.
6. Harvested and seeded mesenchymal colonies on Fibronectin/Collagen I coated (0.67 μg/cm$^2$ Fibronectin, 1.2 μg/cm$^2$ Collagen I) plastic ware in M-SFEM and incubated at 37° C., 5% $CO_2$, 20% $O_2$ (normoxic) for 3 days to produce MSCs (Passage 0).
7. Harvested colonies and seeded as single cells (Passage 1) at 1.3×10$^4$ cells/cm$^2$ on Fibronectin/Collagen 1 coated plastic ware in M-SFEM and incubated at 37° C., 5% $CO_2$, 20% $O_2$ (normoxic) for 3 days.
8. Harvested and seeded as single cells (Passage 2) at 1.3×10$^4$ cells/cm$^2$ on Fibronectin/Collagen 1 coated plastic ware in M-SFEM and incubated at 37° C., 5% $CO_2$, 20% $O_2$ (normoxic) for 3 days.
9. Harvested and seeded as single cells (Passage 3) at 1.3×10$^4$ cells/cm$^2$ on Fibronectin/Collagen 1 coated plastic ware in M-SFEM and incubated at 37° C., 5% $CO_2$, 20% $O_2$ (normoxic) for 3 days.
10. Harvested and seeded as single cells (Passage 4) at 1.3×10$^4$ cells/cm$^2$ on Fibronectin/Collagen 1 coated plastic ware in M-SFEM and incubated at 37° C., 5% $CO_2$, 20% $O_2$ (normoxic) for 3 days.
11. Harvested and seeded as single cells (Passage 5) at 1.3×10$^4$ cells/cm$^2$ on Fibronectin/Collagen 1 coated plastic ware in M-SFEM and incubated at 37° C., 5% $CO_2$, 20% $O_2$ (normoxic) for 3 days.
12. Harvested as single cells and froze final product.

Two experiments (TC-A-96 and DAD-V-90) were executed to investigate the impact of supplementing M-CFM with PDGF-BB (10 ng/mL) and/or LiCl (1 mM) on T cell suppression of iPSC-derived MCA-MSCs. T cell suppression was evaluated generated using Waisman Biomanufacturing's ImmunoPotency Assay (IPA).

As outlined in Table 7, the following combinations of platelet-derived growth factor (PDGF) and LiCl were evaluated: PDGF+/LiCl+, PDGF−/LiCl−, PDGF+/LiCl− and PDGF−/LiCl+. Note that two different Dneg1 seed densities (5×10$^3$ cells/cm$^2$ and 1×10$^4$ cells/cm$^2$) and two different concentrations of activin A (AA) in the Differentiation Medium (1× AA=15 ng/mL and 0.1× AA=1.5 ng/mL) were compared in the TC-A-96 experiment. A single Dneg1 seed density (5×10 e$^3$ cells/cm$^2$) and activin A concentration (1.5 ng/mL) were used in the DAD-V-90 experiment. Also note that a single leukopak (LPK7) was used in the first IPA (IPA 1) and two leukopaks (LPK7 and LPK8) were used in the second IPA (IPA 2).

This assay is designed to assess the degree to which each MSC line can suppress the proliferation of T helper (CD4$^+$) lymphocytes. Cryopreserved MSCs were tested using cryopreserved leukocytes purified from the peripheral blood of healthy individuals (peripheral blood mononucleocyte cells (PBMC) derived from Leucopaks (LPK)). As such, LPK cell population variation is expected from donor to donor. Each MCA-MSC test sample was tested against the PMBC from two different individuals for clinical grade material with the option to limit testing to a single PMBC sample for research grade material. The assay for each MCA-MSC test sample was run in conjunction with a reference standard MSC line to ensure assay integrity/reproducibility and to normalize test samples. The assay is described in Bloom et al. *Cytotherapy*, 2015, 17(2):140-51.

In brief, test MCA-MSCs were exposed to 21 Gy of gamma irradiation. In a 48-well tissue culture plate 4×10 e$^5$, 2×10 e$^5$, 4×10 e$^4$, and 2×10 e$^4$ irradiated MCA-MSCs were plated into individual wells. PMBC were separately labelled with carboxyfluorescein succinimidyl ester. Labelled PMBC cells are plated at 4×10$^5$ cells per well containing the MCA-MSCs above. This results in titrated PBMC:MCA-MSC ratios of 1:1, 1:0.5, 1:0.1, and 1:0.05. An additional well was plated with stimulated PBMCs alone, another with MCA-MSCs alone, and another 1:0.05 ratio without stimulation, all which serve as controls. Subsequently, T cell-stimulatory monoclonal antibodies, anti-human CD3-epilson and anti-human CD28 (R&D Systems, Inc., Minneapolis, Minn.), were added to each well.

On day four of culture, cells were harvested from individual wells. Cells from each well were incubated with allophycocyanin-labelled anti-human CD4. CD4$^+$ cells were then analysed for proliferation via carboxyfluorescein intensity using a flow cytometer. The MCA-MSC alone control served to gate out MCA-MSCs from co-culture wells. The PBMC alone control served as the positive control for maximum T cell proliferation against which the degree of MCA-MSC mediated suppression is measured. The non-stimulated 1:0.05 ratio well was used to generate a negative control gate against which proliferation was measured.

From test sample ratios a best fit curve was used to generate IC50 values. The IC50 values were normalized to the reference standard (IC50 Ref Std/IC50 Test Sample). This normalized IC50 yields larger values for more potent (more suppressive) samples and smaller values for less potent samples.

Results

IC50 data presented in Table 7 show that M-CFM supplemented with LiCl, but excluding PDGF (i.e. PDGF−/LiCl+) was optimal for differentiating iPSCs to produce iPSC-MSCs that are immunomodulatory. Furthermore, a lower concentration of activin A also improved the immunosuppression of iPSC-derived MCA-MSCs.

TABLE 7

ImmunoPotency Assay

| IC50 (LPK7) | IC50 (LPK8) | Sample | PDGF | LiCl | Activin A | Seed Density (D2) |
|---|---|---|---|---|---|---|
| Not Applicable | not suppressive | TC-A-96-B3 | + | + | 0.1X (1.5 ng/mL) | $5 \times 10^3$ cells/cm$^2$ |
| Not Applicable | 0.17 | TC-A-96-B1 | + | + | 1X (15 ng/mL) | $5 \times 10^3$ cells/cm$^2$ |
| Not Applicable | 0.17 | DAD-V-90-4 | + | + | 0.1X (1.5 ng/mL) | $5 \times 10^3$ cells/cm$^2$ |
| Not Applicable | 0.19 | TC-A-96-D3 | + | + | 0.1X (1.5 ng/mL) | $1 \times 10^4$ cells/cm$^2$ |
| Not Applicable | 0.36 | DAD-V-90-2 | + | − | 0.1X (1.5 ng/mL) | $5 \times 10^3$ cells/cm$^2$ |
| Not Applicable | 0.57 | DAD-V-90-1 | − | − | 0.1X (1.5 ng/mL) | $5 \times 10^3$ cells/cm$^2$ |
| 0.39 | 0.54 | TC-A-96-B2 | − | + | 1X (15 ng/mL) | $5 \times 10^3$ cells/cm$^2$ |
| 0.37 | 0.58 | TC-A-96-D2 | − | + | 1X (15 ng/mL) | $1 \times 10^4$ cells/cm$^2$ |
| 0.69 | 0.93 | DAD-V-90-3 | − | + | 0.1X (1.5 ng/mL) | $5 \times 10^3$ cells/cm$^2$ |

MCA-MSCs produced according to this example exhibit a CD73$^+$CD105$^+$CD90$^+$CD146$^+$CD44$^+$CD10$^+$CD31$^-$CD45$^-$ phenotype.

Example 3. MCA-MSC MicroRA Analysis

The MCA-MSC produced according to Example 2 underwent analysis against a microRNA (miRNA) microarray comprising 1194 miRNAs and a proprietary miRNA panel consisting of miR-127-3p, miR-145-5p, miR-181b-5p, miR-214-3p, miR-299-5p, validated against 71 MSC samples and 94 non-MSC samples.

The MCA-MSC produced according to Example 2 expressed each of miR-145-5p, miR-181b-5p, and miR-214-3p, but not miR-127-3p and miR-299-5p.

A principal component analysis of the 233 miRNAs of the microarray reliably detected in the normalised data (present in at least one sample tested) generated for all the samples tested demonstrated that the MCA-MSC produced according to Example 2 was distinct from each of the other 71 MSC samples.

Example 4. Treating AAD/Asthma In Vivo

Methods and Materials

Animals

Six-to-eight week-old female Balb/c mice were obtained from Monash Animal Services (Monash University, Clayton, Victoria, Australia) and housed under a controlled environment, on a 12 hour light/12 hour dark lighting cycle with free access to water and lab chow (Barastock Stockfeeds, Pakenham, Victoria, Australia). All mice were provided an acclimatization period of 4-5 days before any experimentation and all procedures performed were approved by a Monash University Animal Ethics Committee (Ethics number: MARP/2016/078), which complies with the Australian Guidelines for the Care and Use of Laboratory Animals for Scientific Purposes.

Induction of Chronic AAD

To assess the effects of MSCs in chronic AAD, an ovalbumin (OVA)-induced model of chronic AAD was established in mice (n=24). Mice were sensitized with two intraperitoneal (IP) injections of 10 μg of Grade V chicken egg OVA (Sigma-Aldrich, MO, USA) and 400 μg of aluminium potassium sulphate adjuvant (alum; AJAX Chemicals, NSW, Australia) on day 0 and 14. They were then challenged by whole body inhalation exposure (nebulization) to aerosolized OVA (2.5% w/v in 0.9% normal saline) for thirty minutes, three times a week, between days 21 and 63, using an ultrasonic nebulizer (Omron NE-U07; Omron, Kyoto, Japan). For control mice (n=24), however, instead of OVA, they were given IP injections of 500 μL 0.9% saline and nebulized with 0.9% saline.

MCA-MSC Treatment Twenty-four hours after the establishment of chronic AAD (on day 64), subgroups of OVA- or saline-sensitized/challenged mice (n=8 mice/group) underwent IV- or IN-administration of MCA-MSCs. In all cases, a fourteen-day treatment period (from days 64-77) was chosen to replicate the time-frame used to evaluate the IN-delivered effects of other stem cells, such as human bone marrow-derived (stromal) MSCs and human amnion epithelial cells, in the OVA-induced chronic model of AAD.

MCA-MSCs were produced according to Examples 1 and 2. A defining characteristic of MSCs is expression of CD73, CD90 and CD105, and MCA-MSCs cells were >99% positive for all three of these markers, but negative for CD43/45 and CD31, confirming the absence of haematopoietic and endothelial lineage cells. All treatments were administered once per week over the treatment period (on days 64 and 71).

On the morning of each scheduled treatment, frozen MCA-MSCs were thawed in a 37° C. water bath, then resuspended as follows: for IV-administration of MCA-MSCs, $1\times10^7$ cells were resuspended in 2 mL of phosphate-buffered saline (PBS). Mice were restrained in a Perspex restrainer and $1\times10^6$ cells/200 µl of PBS were injected into the tail vein of saline- or OVA-sentisized/challenged mice. For IN-administration of MCA-MSCs, $1\times10^7$ cells were resuspended in 0.5 mL of PBS. Mice were lightly anaesthetised with isoflurane (Baxter Health Care, NSW, Australia) and held in a semi-supine position while intranasal instillation took place. $1\times10^6$ cells/50 µl of PBS were then IN-administered to the mice; 25 µL in each nostril using an automatic pipette.

Invasive Plethysmography

On day 78 (7 days following the last treatment of MCA-MSCs) mice were anaesthetized with ketamine (10 mg/kg body weight) and xylazine (2 mg/kg body weight) in 0.9% saline. Tracheostomy was then performed on all mice with an 18 gauge tracheostomy tube. Mice were then placed in the chamber of the Buxco FinePointe Plethysmograph (Buxco, Research Systems, Wilmington, N.C., USA) and ventilated. Airway resistance of each mouse was then measured in response to increasing doses of nebulised methacholine (methacholine; Sigma-Aldrich, MO, USA) dissolved in PBS and delivered intratracheally from 6.25-50 mg/mL over 4 doses to elicit bronchoconstriction and evaluate AHR. The change in airway resistance (the maximum airway resistance after each dose minus the baseline resistance to PBS alone) was plotted against the corresponding dose of methacholine.

Tissue Collection

Following invasive plethysmography, lung tissues from each animal were isolated and rinsed in cold PBS before being divided into four separate lobes. The largest lobe was fixed in 10% neutral buffered formaldehyde overnight and processed to be cut and embedded in paraffin wax (for histological and immnunohistochemical analysis of various end-points). The remaining three lobes were snap-frozen in liquid nitrogen for various other assays.

Lung Histopathology

Once the largest lobe from each mouse was paraffin-embedded, each tissue block was serially-sectioned (3 µm thickness) and placed on charged Mikro Glass slides (Grale Scientific, Ringwood, Victoria, Australia) and subjected to various histological stains or immunohistochemistry. For assessment of inflammation score, epithelial thickness and sub-epithelial extracellular matrix (ECM) deposition, one section (per slide) from each mouse underwent Masson's trichrome staining. For assessment of goblet cell metaplasia, a second set of slides underwent Alcian blue periodic acid Schiff (ABPAS) staining. The Masson trichrome and ABPAS-stained sections were morphometrically analyzed, as detailed below.

Immunohistoahemistry (IHC)

IHC was used to detect TGF-β1 (using a polyclonal antibody; sc-146; Santa Cruz Biotechnology, Santa Cruz, Calif., USA; 1:1000 dilution) or α-smooth muscle actin (α-SMA; a marker of myofibroblast differentiation; using a monoclonal antibody; M0851; DAKO, Glostrup, Denmark; 1:200 dilution). Primary antibody staining was detected using the DAKO EnVision anti-rabbit or anti-mouse kits and 3,3'-Diaminobenzidine (DAB) chromogen, while negative controls, which were exposed to the EnVision kits in the absence of any primary antibody, were also included. All slides were then counter-stained with haematoxylin and scanned by Monash Histology Services using ScanScope AT Turbo (Aperio, Calif., USA) for morphometric analysis.

Morphametric Analysis

Masson's trichrome-, ABPAS- and IHC-stained slides underwent morphometric analysis as follows. Five airways (of 150-300 µm in diameter) per section were randomly selected and analyzed using Aperio ImageScope software (Aperio, Calif., USA). Masson's trichrome-stained slides underwent semi-quantitative peri-bronchiolar inflammation scoring, where the experimenter was blinded and scored individual airways from 0 (no detectable inflammation surrounding the airway) to 4 (widespread and massive inflammatory cell aggregates, pooled size~0.6 $mm^2$). Masson's trichrome-stained slides also underwent analysis for epithelial thickness and subepithelial ECM deposition by measuring the thickness of the epithelium and the subepithelial ECM layer (stained blue); which were expressed as $\mu m^2/\mu m$ of basement membrane (BM) length.

ABPAS-, α-SMA-stained slides were analyzed for goblet cell metaplasia and sub-epithelial myofibroblast number, respectively, by counting the number of positively stained goblet cells or α-SMA-positive cells per 100 µm of BM length. TGF-β1-stained slides were analyzed for TGF-β1 protein expression by running an algorithm to assess strong positively-stained pixels within the airway. Results were expressed as the number of strong positive pixels per total area ($mm^2$) of airway; and then relative to that of the saline-treated control group, which was expressed as 1.

Hydroxyproline Assay

The second largest lung lobe from each mouse was processed as described before for the measurement of hydroxyproline content (Royce, S. G. et al., (2013) *Clin. Sci.* 124, 41-51), which was determined from a standard curve of purified trans-4-hydroxy-L-proline (Sigma-Aldrich). Hydroxyproline values were multiplied by a factor of 6.94 (based on hydroxyproline representing ~14.4% of the amino acid composition of collagen in most mammalian tissues) to extrapolate total collagen content, which in turn was divided by the dry weight of each corresponding tissue to yield percent collagen concentration.

Gelatin Zymography

The third largest lung lobe from each mouse was processed as detailed previously for extraction of proteins containing matrix metalloproteinases (MMPs) (Woessner, J. F., (1995) *Methods Enzymol.* 248, 510-528) before equal aliquots of total protein (10 µg per sample) were assessed on 7.5% acrylamide gels containing 10 µg/ml gelatin. Gelatinolytic activity was visualized as clear bands. Densitometry of MMP-9 (the predominant gelatinase in the lung of female Balb/c mice) was performed using a GS710 Densitometer (Bio-Rad Laboratories, Gladesville, NSW, Australia) and Quantity-One software (Bio-Rad). The relative mean±SEM optical density (OD) of MMP-9 was then graphed.

Statistical Analysis

All statistical analysis was performed using GraphPad Prism v6.0 (GraphPad Software Inc., La Jolla, Calif., USA) and expressed as the mean±SEM. AHR results were analyzed by a two-way ANOVA with Bonferroni post-hoc test. The remaining data was analyzed by a one-way ANOVA with Neuman-Keuls post-hoc test for multiple comparisons between groups. In each case, data were considered significant at $P<0.05$.

Results

Effects of MCA-MSCs on AI

Figure 1:
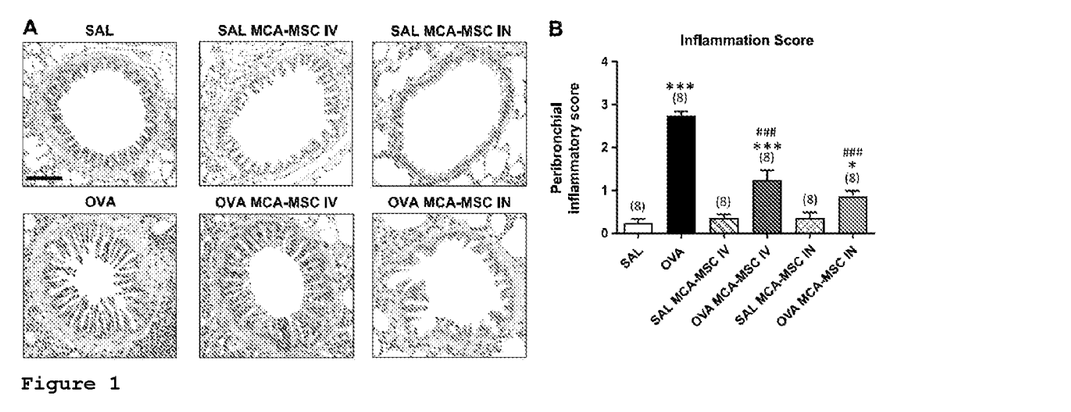
FIG. 1 shows effects of MCA-MSCs on peribronchial inflammation score according to Example 4. A) Representative photomicrographs of hematoxylin and eosin (H&E)-stained lung sections from each of the groups studied show the extent of bronchial wall inflammatory cell infiltration present within and around the airway epithelial layer. Scale bar=50 μm. B) Also shown is the mean±SEM inflammation score from five airways/mouse, n=8 mice/group, where sections were scored for the number and distribution of inflammatory aggregates on a scale of 0 (no apparent inflammation) to 4 (severe inflammation). *$P<0.05$, ***$P<0.001$ vs saline (SAL) group; ####$P<0.001$ vs OVA group.

AI was semi-quantitated from H&E-stained lung sections using an inflammation scoring system (from 0-4). The peribronchial inflammatory score of OVA-injured mice (2.75±0.09) was significantly higher than that scored for the saline (SAL)-sensitized/challenged controls (0.25±0.09;

P<0.001 vs SAL group) (FIG. 1). The elevated level of inflammation in the OVA group confirmed that these mice had been successfully sensitized and challenged with OVA.

Administration of MCA-MSCs significantly reduced the OVA-induced peribronchial inflammatory cell infiltration (1.25±0.23; P<0.001 vs OVA group) without affecting basal inflammation score when administered to SAL-control mice (FIG. 1A, FIG. 1B). However, treatment with MCA-MSCs was not able to fully reduce AI back to that measured in SAL-control mice (P<0.05 vs SAL group for treatment administering MCA-MSCs to OVA-injured mice).

Effects of MCA-MSCs on AWR

Goblet Cell Metaplasia

Figure 2:
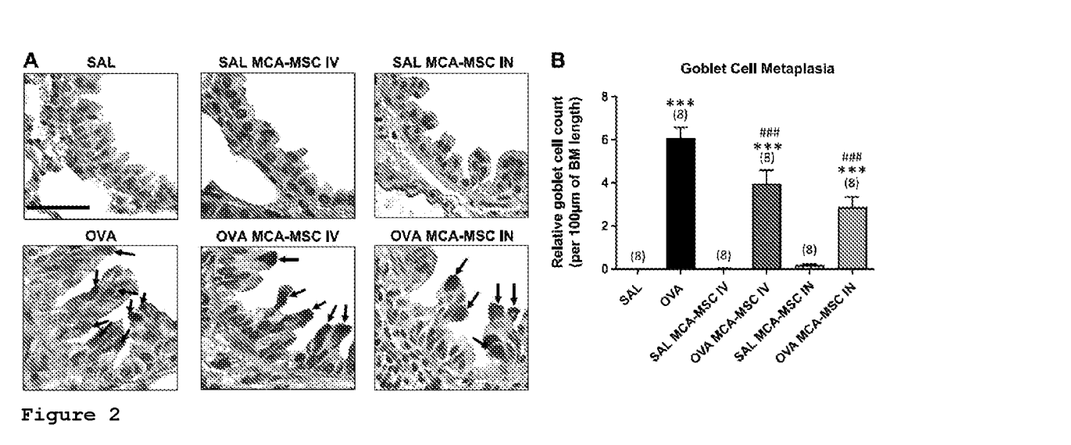
FIG. 2 shows effects of MCA-MSCs on goblet cell metaplasia according to Example 4. A) Representative photomicrographs of Alcian blue periodic acid Schiff (ABPAS)-stained lung sections from each of the groups studied show the extent of goblet cells (indicated by arrows in OVA-injured mice only) within the airway epithelial layer. Scale bar=25 μm. B) Also shown is the mean±SEM goblet cell count from five airways/mouse, n=8 mice/group. ***$P<0.001$ vs saline (SAL) group; ##$P<0.01$, ####$P<0.001$ vs OVA group.

Goblet cell metaplasia was morphometrically assessed from ABPAS-stained lung sections and expressed as number of goblet cells/100 μm of BM length (FIG. 2). OVA-treated mice had significantly increased goblet cell numbers (6.08±0.52) compared to their SAL-control counterparts (0.001±0.00; P<0.001 vs SAL group; FIG. 2A, FIG. 2B). Administration of MCA-MSCs was able to significantly, although not totally, reduce the OVA-induced promotion of goblet cell numbers (3.97±0.64 to 2.89±0.48, P<0.01 vs OVA group; FIG. 2A, FIG. 2B). However, MCA-MSC delivery did not restore the OVA-induced goblet cell metaplasia to that measured in SAL-controls (both P<0.001 vs SAL group), but did not affect goblet cell numbers in SAL-treated mice.

Airway Epithelial Thickness

Figure 3:
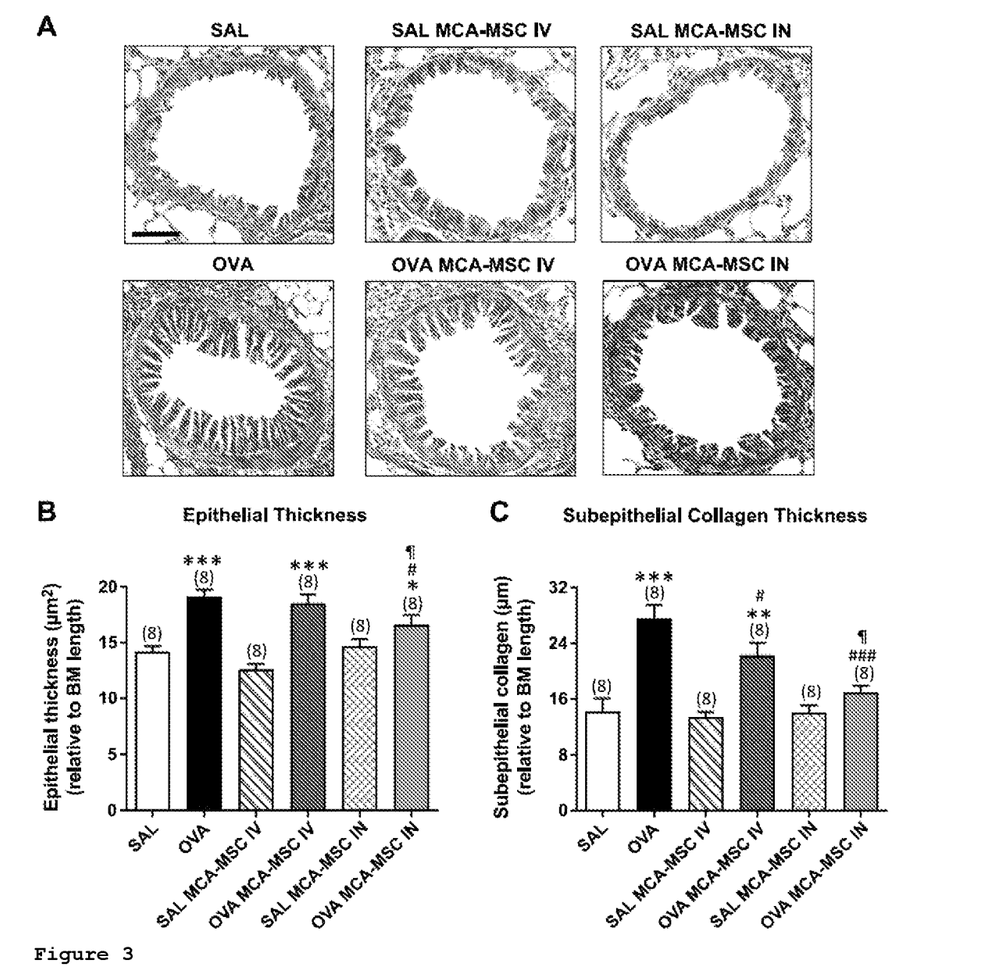
FIG. 3 shows effects of MCA-MSCs on airway epithelial thickness and subepithelial collagen deposition (fibrosis) according to Example 4. A) Representative photomicrographs of Masson trichrome-stained lung sections from each of the groups studied show the extent of airway epithelial thickness and subepithelial collagen thickness (blue staining). Scale bar=50 μm. Also shown is the mean±SEM B) epithelial thickness ($\mu m^2$) and C) subepithelial collagen thickness (μm) relative to basement membrane (BM) length from five airways/mouse, n=8 mice/group. *$P<0.05$, $P<0.01$, *$P<0.001$ vs saline (SAL) group; #$P<0.05$, ####$P<0.001$ vs OVA group; ¶$P<0.05$ vs OVA MCA-MSC IV group.

Airway epithelial thickness was morphometrically assessed from Masson's trichrome stained lung sections and expressed as $\mu m^2/\mu m$ BM length (FIG. 3). The epithelial thickness of OVA treated mice (19.16±0.63) was significantly higher than that measured in SAL-controls (14.28±0.45; P<0.001 vs SAL group; FIG. 3A, FIG. 3B). Delivery of MCA-MSCs significantly, although not totally, decreased the thickness of the epithelium (18.59±0.77 to 16.67±0.87) from that measured in the OVA group (P<0.05 vs OVA group; P<0.05 vs SAL group; FIG. 3A, FIG. 3B). Importantly, MCA-MSC treatment did not affect basal epithelial thickness in SAL-control mice.

Subepithelial Collagen Deposition

Subepithelial collagen deposition was assessed morphometrically from Masson trichrome-stained lung sections and expressed as $\mu m^2/\mu m$ BM length (FIG. 3); and significantly elevated in the OVA-injured mice (27.63±0.66) compared to that in SAL-controls (14.31±1.87; P<0.001 vs SAL group; FIG. 3A, FIG. 3C). Delivery of MCA-MSCs reduced the aberrant OVA-induced promotion of subepithelial collagen deposition (22.39±1.78 to 16.98±0.98; P<0.05 vs OVA group; FIG. 3A, FIG. 3C).

Figure 4:
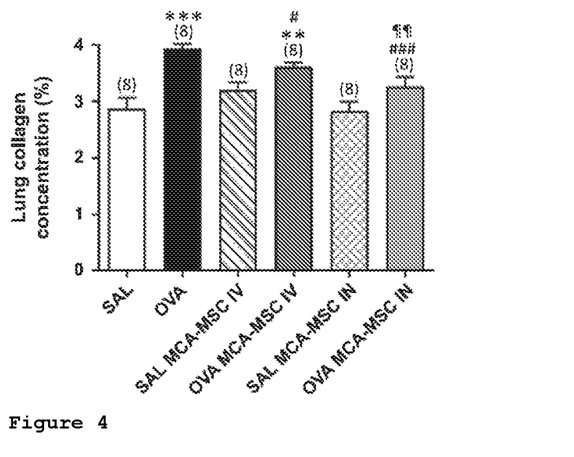
FIG. 4 shows effects of MCA-MSCs on total lung collagen concentration (another measure of fibrosis) according to Example 4. Shown is the mean±SEM total lung collagen concentration (% lung collagen content/dry weight tissue) from each of the groups studied; measured from the second largest lung lobe per mouse, from n=8 mice/group. $P<0.01$, *$P<0.001$ vs saline (SAL) group; #$P<0.05$, ####$P<0.001$ vs OVA group; ¶¶$P<0.05$ vs OVA MCA-MSC IV group.

Total Lung Collagen Concentration (Fibrosis) Total lung collagen concentration (% collagen concentration/dry weight lung tissue) was extrapolated from hydroxyproline levels present within the second largest lung lobe of each mouse and used as a measure of fibrosis (FIG. 4); and was significantly increased in OVA-injured mice (3.94±0.09%) compared to that measured in SAL-controls (2.89±0.18%; P<0.001 vs SAL group). Administration of MCA-MSCs to OVA-injured mice reduced fibrosis in the lungs (3.26±0.17% to 3.62±0.07%; P<0.05 vs OVA group; FIG. 4).

Airway TGF-β1 Expression

Figure 5:
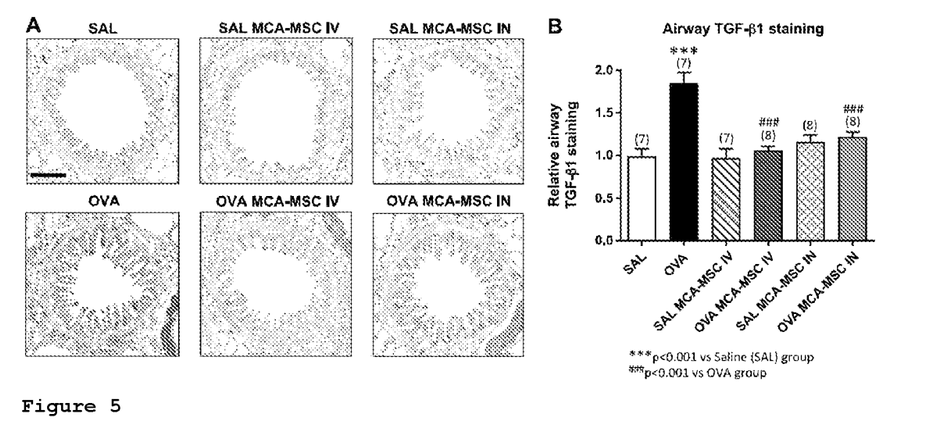
FIG. 5 shows effects of MCA-MSCs on airway TGF-β1 (pro-fibrotic cytokine) expression according to Example 4. A) Representative photomicrographs of immnunohistochemistry (IHC)-stained lung sections from each group studied show the extent of TGF-β1 staining/expression within and around the airway epithelial layer. Scale bar=50 μm. B) Also shown is the relative mean±SEM TGF-β1 staining (expressed as %/field) from five airways/mouse, n=7-8 mice/group. ***$P<0.001$ vs saline (SAL) group; ####$P<0.001$ vs OVA group.

To determine the mechanisms by which MCA-MSCs were able to reverse OVA-induced sub-epithelial and total collagen deposition (fibrosis), the relative changes in airway TGF-β1 (pro-fibrotic cytokine) expression levels were morphometrically assessed from IHC-stained lung sections and expressed as % staining per airway analyzed (FIG. 5). Airway TGF-β1 expression was significantly increased in OVA-injured mice (1.85±0.13) compared to that measured in SAL-controls (1.00±0.08; P<0.001 vs SAL group; FIG. 5A, FIG. 5B). Delivery of MCA-MSCs to OVA-injured mice reversed aberrant airway TGF-β1 expression levels back to that measured in SAL-controls (1.06±0.05 to 1.22±0.05; P<0.001 vs OVA group; not different to SAL group) without affecting basal airway TGF-β1 expression levels when administered to SAL-control mice (FIG. 5A, FIG. 5B).

Subepithelial Myofibroblast Density

Figure 6:
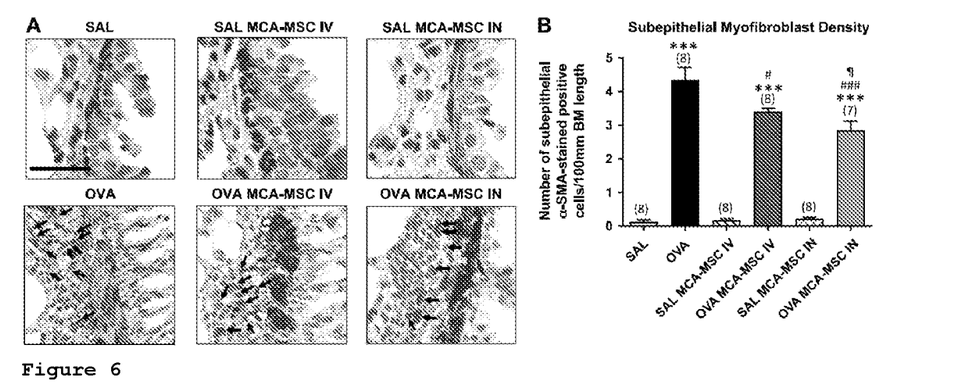
FIG. 6 shows effects of MCA-MSCs on subepithelial myofibroblast (key fibrosis-producing cell) density according to Example 4. A) Representative photomicrographs of IHC-stained lung sections from each group studied show the extent of α-SMA-stained myofibroblast density (as indicated by the arrows) within the airway subepithelial layer. Scale bar=25 μm. B) Also shown is the mean±SEM number of myofibroblasts (per 100 μm BM length) from five airways/mouse, n=7-8 mice/group. ***$P<0.001$ vs saline (SAL) group; #$P<0.05$, ####$P<0.001$ vs OVA group; ¶$P<0.05$ vs OVA MCA-MSC IV group.

Changes in α-SMA-stained subepithelial myofibroblast density were also morphometrically assessed from IHC-stained lung sections and expressed as the number of myofibroblasts/100 μm of BM length (FIG. 6). Trace amounts of subepithelial α-SMA-positive myofibroblasts were detected in SAL-control mice (0.14±0.05), while OVA-injured mice had a ~30-fold increase in myofibroblast density (4.37±0.37; P<0.001 vs SAL group; FIG. 6A, FIG. 6B). Administration of MCA-MSCs reduced the OVA-induced increase in subepithelial myofibroblast density (2.86±0.27 to 3.42±0.09; P<0.05 vs OVA group) in the absence of any effects on basal myofibroblast numbers when administered to SAL-control mice (FIG. 6A, FIG. 6B). However, MCA-MSC administration did not fully reverse the aberrant subepithelial myofibroblast burden back to that measured in SAL-control mice (both P<0.001 vs SAL group; FIG. 6A, FIG. 6B).

Lung Gelatinase Expression

Figure 7:
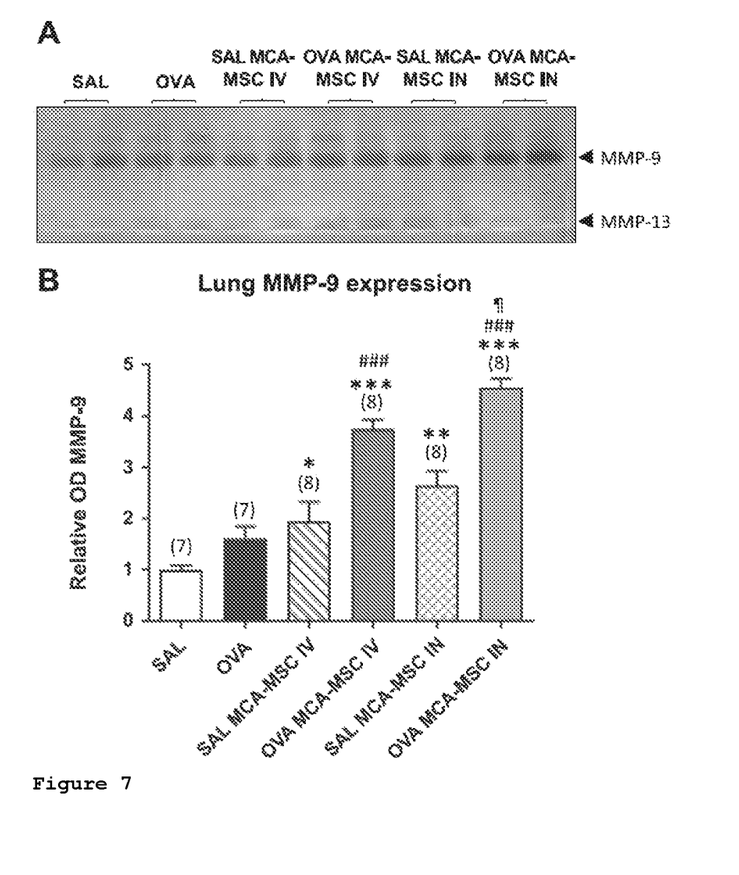
FIG. 7 shows effects of MCA-MSCs on MMP-9 (a collagen-degrading enzyme) levels according to Example 4. A) A representative gelatin zymograph (inverted image) shows the relative expression levels of lung MMP-9 (gelatinase B; 92 kDa) and MMP-13 (collagenase-3; ~55 kDa) in the each of the groups studied. In each case, 10 μg of total protein per sample were loaded onto zymographs for analysis; and separate zymographs analyzing five-six additional samples per group produced similar results. B) Also shown is the relative mean±SEM optical density (OD) MMP-9 (which is the most abundantly expressed gelatinase in the lung of female Balb/c mice) from n=7-8 mice/group. *$P<0.05$, $P<0.01$, *$P<0.001$ vs saline (SAL) group; ####$P<0.001$ vs OVA group; †$P<0.05$ vs OVA MCA-MSC IV group.

We also determined if the MCA-MSC-mediated reversal of OVA-induced airway/lung fibrosis was associated with their ability to influence collagen-degrading MMP levels. Gelatin zymography demonstrated that the lungs of female Balb/c mice predominantly expressed MMP-9 (gelatinase B) and to a lesser extent, MMP-13 (collagenase-3) (FIG. 7). Relative MMP-9 expression levels in OVA-injured mice (1.62±0.22) were not significantly different to that measured in SAL-control animals (1.00±0.09) (FIG. 7A; FIG. 7B). In comparison, administration of MCA-MSCs to OVA injured mice markedly increased MMP-9 levels (3.77±0.18 to 4.56±0.20; P<0.05 vs OVA MCA-MSC group) by ~1.3 and ~1.8-fold over what was measured in OVA-treated mice alone (P<0.001 vs OVA group; P<0.001 vs SAL group; FIG. 7A; FIG. 7B). Interestingly, delivery of MCA-MSCs to SAL-treated mice also significantly increased MMP-9 levels (1.95±0.38 to 2.65±0.30; P<0.05 vs SAL group).

Effects of MCA-MSCs on AHR

AHR was assessed by invasive plethysmography in response to increasing concentrations of nebulized methacholine—a bronchoconstrictor (FIG. 8). Expectedly, OVA-treated mice had significantly elevated AHR compared to that measured in SAL-controls (P<0.001 vs SAL group; FIG. 8). Delivery of MCA-MSCs reversed the OVA-induced increase in AHR (P<0.05 vs OVA group; FIG. 8). As with most other end-points measured, MCA-MSC delivery did not affect basal AHR measurements when administered to SAL-control mice (FIG. 8).

Discussion

This study aimed to assess the therapeutic potential of novel iPSC-derived MCA-MSCs against the three central components of chronic AAD/asthma pathogenesis: AI, AWR and AHR, when therapeutically given to established disease pathology.

Administration of MCA-MSCs protected against the established AI, AWR (goblet cell metaplasia, aberrant airway TGF-β1 levels, subepithelial myofibroblast and collagen accumulation, total lung collagen concentration) and AHR that was induced by repeated OVA sensitization and challenge to mice (Table 8). This resulted in reversal of aberrant airway TGF-β1 levels, airway/lung fibrosis and AHR over a two-week (once weekly) treatment period, and a significant increase in collagen-degrading MMP-9 levels by delivery of MCA-MSCs (Table 8). Just as importantly, MCA-MSC administration was not found to affect basal expression of the parameters measured, suggesting that delivery of MCA-MSC offers a safe and most effective means of treating the central components of AAD/asthma.

which the IN-delivery of bone marrow-MSCs alone had no effect on epithelial thickness. In that study, epithelial thickness was not affected by a decrease in AI. Hence, the difference observed between MCA-MSCs and bone marrow-MSCs appears due to an active property of MCA-MSCs themselves, rather than a passive effect produced by their ability to attenuate AI.

Furthermore, in another study, administration of an epithelial factor repair peptide (trefoil factor-2) reduced epithelial thickness to the same extent as combination treatment

TABLE 8

Summary MCA-MSC effects on the pathologies of chronic AAD

| Key features of human asthma | OVA | SAL MCA-MSCs IV | OVA MCA-MSCs IV | SAL MCA-MSCs IN | OVA MCA-MSCs IN |
|---|---|---|---|---|---|
| AI | ↑↑↑ | — | ↓ | — | ↓↓ |
| Goblet cell metaplasia | ↑↑↑ | — | ↓ | — | ↓↓ |
| Epithelial thickness | ↑↑↑ | — | — | — | ↓↓* |
| Subepithelial collagen | ↑↑↑ | — | ↓ | — | ↓↓↓* |
| Total lung collagen | ↑↑↑ | — | ↓ | — | ↓↓↓* |
| Airway TGF-β1 levels | ↑↑↑ | — | ↓↓↓ | — | ↓↓↓ |
| Subepithelial myofibroblast density | ↑↑↑ | — | ↓ | — | ↓↓* |
| Lung MMP-9 levels | — | ↑ | ↑↑↑ | ↑↑ | ↑↑↑* |
| AHR | ↑↑↑ | — | ↓↓ | — | ↓↓↓** |

In Table 8, the arrows in the OVA, SAL MCA-MSC IV and SAL MCA-MSC IN columns are reflective of changes to that measured in saline (SAL)-treated mice, whereas the arrows in the OVA MCA-MSC IV and OVA MCA-MSC IN groups are reflective of changes to that in the OVA alone group.
(—) implies no change compared to SAL or OVA-treated mice, respectively.
*$P < 0.05$,
**$P < 0.01$ vs OVA MCA-MSC IV group.

The inflammatory component of asthma contributes to airway obstruction. The Th2-skewed inflammation results in the elevation of a particular subset of cytokines, including interleukin (IL)-13, and the induction of goblet cell metaplasia.

Consistent with these findings, previous studies have shown that IV-injection of iPSC-derived MSCs (not MCA-MSCs as disclosed herein) could partially decrease airway inflammatory score in an acute OVA model by suppressing the levels of the Th2 cytokines, IL-4, IL-5 and IL-13. The systemic effects of MCA-MSCs may even be linked to their ability to activate regulatory T cells through direct cell-cell contact. However, the current findings that MCA-MSCs markedly suppressed AI by ~75% and goblet cell metaplasia by ~50% indicates that MCA-MSCs mediate greater immunomodulatory properties compared to MSCs derived from the human bone marrow or adipose tissue.

Direct administration of MCA-MSCs into the airways/lung allows the protective factors they secrete to remain in the pulmonary environment. Furthermore, directly administered MCA-MSCs are more likely to remain in the inflamed lungs and have greater protective effects against allergen exposure mediated through the suppression of antigen presentation cells including alveolar macrophages and dendritic cells.

Along with goblet cell metaplasia, epithelial proliferation is a major contributor to epithelial remodelling in asthma. Diminution in epithelial barrier function and desquamation culminate as epithelial proliferation. This proliferation is particularly extensive in severe asthma where expansion of the epithelium leads to airway obstruction. Given that this reprogramming occurs early in the pathogenesis of asthma, asthma therapy should target the epithelium. Delivery of MCA-MCSs resulted in a decreased epithelial thickness, despite offering similar reductions in AI. This contrasts with previous findings related to bone marrow-derived MSCs, in with an anti-fibrotic and a corticosteroid, despite a greater decrease in AI offered by the combination treatment. As such, the reduction in epithelial proliferation was not mediated by a reduction in inflammation.

With this additional evidence, the present findings indicate that delivery of MCA-MSCs allows i) sufficient accumulation of paracrine factors that reduce epithelial thickness and/or ii) these cells to come into direct contact with the damaged epithelium and mediate a reversal in its proliferation. This decrease in the epithelial thickness and goblet cell metaplasia produced by MCA-MSCs is the first evidence of reversed AWR.

The culmination of a number of factors, including mechanical insults and allergens can contribute to the destruction of the pulmonary architecture and airway function leading to AWR, in addition to AI. Damage due to allergens or from heritable susceptibility causes the lungs to undergo endogenous processes of remodelling in an effort to self-repair structure and function of the airways, and these reparative processes result in aberrant wound healing, eventually leading to fibrosis. Fibrosis was evident in the OVA-sensitized airways, which showed an elevation in aberrant subepithelial and total collagen levels. Delivery of MCA-MSCs significantly reduced both aberrant subepithelial and total collagen deposition, and in some cases completely reversed this aberrant collagen deposition back to the levels seen in the uninjured-saline-treated group. These results were unexpected as previous studies showed that the OVA-induced promotion of subepithelial and total collagen deposition could only be fully reversed when stem cell-based treatments were co-administered with an anti-fibrotic drug. In these combination treatment studies, it was proposed that the anti-fibrotic drug would create a more favourable environment in which stem cell-based therapies could be introduced, thus aiding stem cell survival and increasing their proliferative and migratory capacity to induce their protective/therapeutic effects. Hence, delivery of MCA-MSCs has similar effects to an anti-fibrotic drug and may possess anti-fibrotic properties similar to fetal fibroblasts, which can facilitate wound healing in the absence of fibrosis.

These results also correspond with the MCA-MSC-induced reduction in epithelial thickness observed. Fibrogenic growth factors are commonly released by epithelial cells in response to epithelial disturbances. In asthma, this response is enhanced, suggesting that subepithelial fibrosis results from a conduit of signals from a defective epithelium to the deeper airway wall. As such, MCA-MSCs could exert their anti-fibrotic effects via immunomodulatory properties and possible secretion of anti-fibrotic mediators given the reduction in subepithelial and total collagen when administered IV.

The key finding of this study was that MCA-MSCs reversed fibrosis and reverted AHR to levels measured in uninjured mice. AHR is driven by airway obstruction, which can be caused by mucus plugging from goblet cell metaplasia and epithelial thickening. In addition, the interaction between AI and fibrosis of the airway wall lead to an environment that elevates AHR. Not only does fibrosis decrease airway compliance in subjects with asthma, but this expansion in ECM leads to the retention of soluble inflammatory mediators and chronic persistence of established AHR. As such, AHR could be reverted to normal uninjured levels mainly by the reduction of subepithelial fibrosis and attenuation of AI and/or by a decrease in airway obstruction mediated by the reduced counts of goblet cells and lower levels of epithelial thickening afforded by MCA-MSCs. As disclosed herein, MCA-MSCs corrected AHR by targeting AWR at a number of levels, in addition to their anti-inflammatory effects.

In conclusion, the present study, the first using MCA-MSCs to treat chronic AAD/asthma, found that MCA-MSCs effectively reduce AI and reverse markers of AWR as well as AHR. Therefore, MCA-MSCs provide a stand-alone therapy for AAD/asthma. MCA-MSCs may also be used as an adjunct therapy for AAD/asthma. MCA-MSCs may provide particular therapeutic benefits to sub-populations of subjects with AAD/asthma who do not respond to current therapy, i.e. corticosteroid or β-agonist therapy.

A striking finding that separates MCA-MSCs from other stem cells studied previously is that other MSCs/stem cells only produced therapeutic effects when administered in combination with other therapeutic agents.

Example 5

Figure 9:
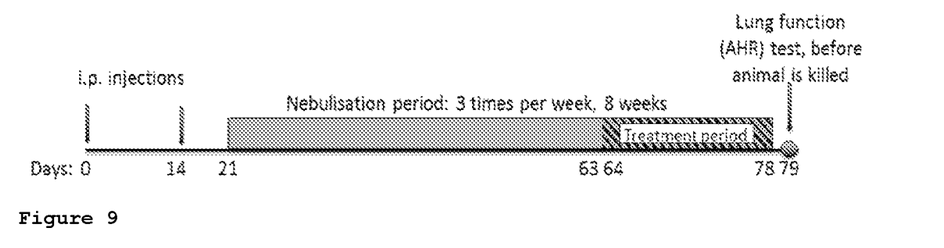
FIG. 9 is a schematic Timeline for the chronic allergic airways disease model of Examples 5 and 6. Treatment is administered from day 64-78 (when lung pathology is established and ongoing).
Figure 10:
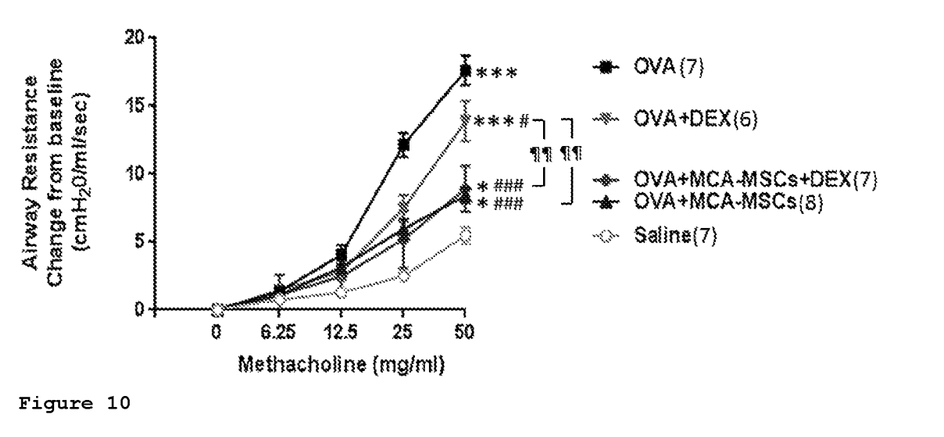
FIG. 10 shows effects on AHR of MCA-MSCs supplemented with dexamethasone (DEX) according to Example 5. Airway resistance (reflecting changes in AHR) was assessed via invasive plethysmography in response to increasing doses of nebulized methacholine (a bronchoconstrictor; and expressed as resistance change from baseline) according to Example 4. Shown is the mean±SEM airway resistance to each dose of methacholine tested; from n=6-8 mice/group. *P<0.05, ***P<0.001 vs saline (SAL) group; #P<0.05, ###P<0.001 vs OVA group; ¶¶P<0.01 vs OVA+ DEX group.

AAD/asthma was induced in groups of 6 to 8 mice in a similar manner as Example 4, except that mice were challenged with a nebulised aerosol solution of ovalbumin for 30 minutes, three times per week for 8 weeks (from days 21 to 77, FIG. 9), instead of for 6 weeks as in Example 4. Mice were randomly assigned to one of five groups: 1 untreated controls (no asthma); 2 untreated sensitised animals (asthma); 3 sensitised animals (asthma), treated with IN infusion of MCA-MSCs; 4 sensitised animals (asthma), treated with IN infusion of dexamethasone (DEX); 5 sensitised animals (asthma), treated with IN infusion of MCA-MSCs+DEX. All MCA-MSC-treated mice received a dose of $10^6$ cells IN on two occasions (once weekly in weeks 9 and 10). DEX (1 mg/kg/day) was administered once daily from weeks 9-11. DEX improved AHR, but MCA-MSCs had a significantly more pronounced effect, with DEX having no additional effect beyond that of MCA-MSCs alone (FIG. 10).

Example 6

The model used in this example was the same as Example 5, the 9 week allergen-induced chronic airways disease model using female Balb/c mice that are most responsive in this model.

The following groups of 7-8 week old female Balb/c mice (n-8 mice/group) were compared in which MCA-MSCs were administered once weekly from weeks 9-11 via intranasal (IN), intravenous (IV), or and endotracheal (ET) administration:

i) saline sensitised/challenged controls;
ii) OVA sensitised/challenged (AAD);
iii) OVA sensitised/challenged+$1 \times 10^6$ MCA-MSCs/mouse by IN administration;
iv) OVA sensitised/challenged+$1 \times 10^6$ MCA-MSCs/mouse by IV administration; and
vi) OVA sensitised/challenged+$1 \times 10^6$ MCA-MSCs/mouse by ET administration.

This design with a 20% SD, provided 90% power to detect a 25% effect with n=8 mice/group.

Figure 11:
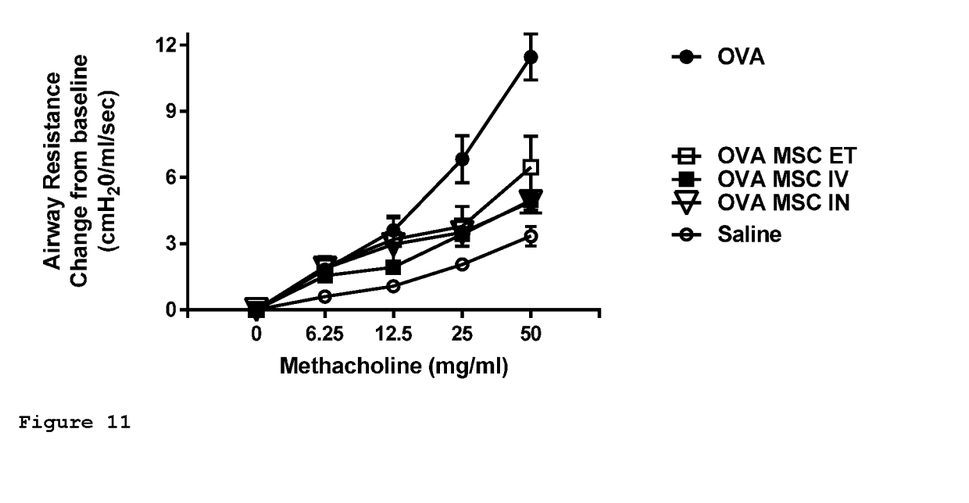
FIG. 11 shows effects on AHR of MCA-MSCs administered intranasally (IN) vs intravenously (IV) vs endotracheally (ET) according to Example 6. Airway resistance (reflecting changes in AHR) was assessed via invasive plethysmography in response to increasing doses of nebulized methacholine (a bronchoconstrictor; and expressed as resistance change from baseline) according to Example 4. Shown is the mean±SEM airway resistance to each dose of methacholine tested; from n=6-8 mice/group. p<0.01, *p<0.001 vs saline-treated group; ##p<0.01 vs OVA group.

Airway hyperresponsiveness (a measure of lung function) was analysed and is reported in FIG. 11.

Mice with OVA-induced chronic AAD had significantly worsened AHR in response to increasing doses of a bronchoconstrictor compared to their saline-treated counterparts. This OVA-induced AHR was significantly decreased by 79-80% by IN or IV administration of MCA-MSCs (once weekly administration from weeks 9-11 in the presence of ongoing OVA-induced injury). There was no significant difference in AHR between mice IN- or IV-treated with MCA-MSCs vs saline-treated controls.

ET administration of MCA-MSCs decreased AHR by 61%—which was still significantly lower than that measured from the OVA group alone, but was also significantly higher than that measured from the saline group.

There was no significant difference in AHR between the IN- vs IV- vs ET-treated groups, indicating that all three modes of MCA-MSC delivery provide a feasible approach of treating chronic AAD/asthma.

Additional endpoints to be analysed include:
i) inflammation score;
ii) goblet cell metaplasia;
iii) epithelial thickness;
iv) epithelial damage;
v) sub-epithelial collagen thickness;
vi) total lung collagen concentration;
vii) epithelial TGF-beta1 staining;
viii) subepithelial myofibroblast density; and
ix) gelatinase (MMP-2 and MMP-9) expression/activity.

The invention claimed is:
1. A method for treating allergic airways disease (AAD) or asthma in a subject, the method comprising administering a mesenchymoangioblast mesenchymal stem cell (MCA-MSC) to the subject, wherein the MCA-MSC expresses miR-145-5p, miR-181b-5p, and miR-214-3p, but not miR-127-3p and miR-299-5p.
2. The method of claim 1, wherein the MCA-MSC has a $CD73^+CD105^+CD90^+CD146^+CD44^+CD10^+CD31^-CD45^-$ phenotype.

3. The method of claim 1, wherein the MCA-MSC is made by a method comprising:
 (a) culturing a primitive mesoderm cell in a mesenchymal-colony forming medium (M-CFM) comprising LiCl and FGF2, but excluding PDGF, under normoxic conditions for sufficient time for a mesenchymal colony to form; and
 (b) culturing the mesenchymal colony of (a) adherently to produce the MCA-MSC.

4. The method of claim 1, wherein the MCA-MSC is administered intravenously or intranasally.

5. The method of claim 1, wherein the MCA-MSC is administered intranasally.

6. The method of claim 1, wherein about $1\times10^6$ MCA-MSCs to about $1\times10^9$ MCA-MSCs.

7. The method of claim 1, wherein the subject is mammalian.

8. The method of claim 1, wherein the subject is human.

9. The method of claim 1, wherein the subject has previously been administered a corticosteroid or a β-agonist for treating asthma.

10. The method of claim 1, wherein the subject has not previously been administered a corticosteroid or a β-agonist for treating asthma.

11. The method of claim 1, wherein the subject has severe asthma or severe-refractory asthma.

12. The method of claim 1, wherein treating AAD or asthma comprises:
 (a) decreasing airway inflammation (AI), airway remodeling (AWR), airway fibrosis, lung fibrosis, goblet cell metaplasia, epithelial thickening, airway transforming growth factor (TGF)-β1 level, subepithelial myofibroblast density, subepithelial collagen concentration, or total lung collagen concentration; or
 (b) increasing lung MMP activity; or
 (c) any combination of any one or more feature of (a) or any combination of any one or more feature of (a) and (b).

13. The method of claim 1, wherein the subject is not administered a corticosteroid or a β-agonist.

14. The method of claim 1, wherein about $10^6$ MCA-MSCs/kg to about $2\times10^8$ MCA-MSCs/kg are administered to the subject.

15. The method of claim 1, wherein the MCA-MSCs are administered to the subject before, during or after development of AAD or asthma.

16. The method of claim 1, wherein about $10^6$ MCA-MSCs to about $2\times10^8$ MCA-MSCs are administered to the subject.

17. The method of claim 1, wherein about $10^8$ MCA-MSCs are administered to the subject.

18. The method of claim 1, wherein about $5\times10^8$ MCA-MSCs are administered to the subject.

19. The method of claim 1, wherein about $10^9$ MCA-MSCs are administered to the subject.

20. The method of claim 1, wherein about $10^6$ MCA-MSCs/kg are administered to the subject.

21. The method of claim 1, wherein about $5\times10^6$ MCA-MSCs/kg are administered to the subject.

22. The method of claim 1, wherein about $10^7$ MCA-MSCs/kg are administered to the subject.

* * * * *